(12) United States Patent
Sata et al.

(10) Patent No.: US 8,932,568 B2
(45) Date of Patent: Jan. 13, 2015

(54) HAIR CONDITIONING COMPOSITION

(75) Inventors: Juri Sata, Wakayama (JP); Yoshinori Tamura, Wakayama (JP); Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 42 days.

(21) Appl. No.: 12/933,626

(22) PCT Filed: Apr. 3, 2009

(86) PCT No.: PCT/JP2009/001563
§ 371 (c)(1),
(2), (4) Date: Sep. 20, 2010

(87) PCT Pub. No.: WO2009/122755
PCT Pub. Date: Oct. 8, 2009

(65) Prior Publication Data
US 2011/0014145 A1  Jan. 20, 2011

(30) Foreign Application Priority Data

Apr. 4, 2008 (JP) .................................. 2008-097832
Apr. 4, 2008 (JP) .................................. 2008-097833
Dec. 25, 2008 (JP) .................................. 2008-329195
Dec. 25, 2008 (JP) .................................. 2008-329616

(51) Int. Cl.
*A61Q 5/12* (2006.01)
*A61K 8/81* (2006.01)
*A61K 8/39* (2006.01)

(52) U.S. Cl.
CPC .... *A61K 8/39* (2013.01); *A61Q 5/12* (2013.01)
USPC .................. 424/70.11; 424/70.27; 424/70.28; 424/70.1

(58) Field of Classification Search
None
See application file for complete search history.

(56) References Cited

U.S. PATENT DOCUMENTS

2009/0124523 A1  5/2009  Dol et al.

FOREIGN PATENT DOCUMENTS

| EP | 1 956 065 A1 | 8/2008 |
|---|---|---|
| EP | 1 972 326 A1 | 9/2008 |
| JP | 59-163303 A | 9/1984 |
| JP | 62-132812 A | 6/1987 |
| JP | 1 106812 | 4/1989 |
| JP | 04-230614 A | 8/1992 |
| JP | 6-298625 A | 10/1994 |
| JP | 06-305939 A | 11/1994 |
| JP | 7 267836 | 10/1995 |
| JP | 2003-286138 A | 10/2003 |
| JP | 2004-359575 A | 12/2004 |
| JP | 2006/045183 A * | 2/2006 |
| JP | 2007 197420 | 8/2007 |
| JP | 2008 163237 | 7/2008 |
| WO | 2007 052657 | 5/2007 |
| WO | 2008 029516 | 3/2008 |
| WO | WO 2008/029516 A1 | 3/2008 |

OTHER PUBLICATIONS 0 312 995
Extended European Search Report issued Jun. 17, 2014 in Patent Application No. 09729185.0.

* cited by examiner

*Primary Examiner* — Abigail Fisher
*Assistant Examiner* — Daniel L Branson
(74) *Attorney, Agent, or Firm* — Oblon, Spivak, McClelland, Maier & Neustadt, L.L.P.

(57) ABSTRACT

Provided is a low odor hair conditioning composition which is free of oily and greasy feel upon finish, and can impart good manageability and moisturized feel. Specifically provided is a hair conditioning composition including a component (A): a compound represented by a general formula (1) $R^1O-(PO)_n/(EO)_m-R^2$ (1), where $R^1$ represents a straight or branched, alkyl or alkenyl group having 8 to 12 carbon atoms, PO represents a propyleneoxy group, EO represents an ethyleneoxy group, an average addition mole number "n" represents a number of 1.5 to 3.0, an average addition mole number "m" represents a number of 0 to 1.0, and $R^2$ represents a hydrogen atom or a methyl group; and a component (B): a surfactant other than the component (A), wherein a content of $R^1OH$, where $R^1$ represents a straight or branched, alkyl or alkenyl group having 8 to 12 carbon atoms, is 80 ppm or less.

20 Claims, No Drawings

HAIR CONDITIONING COMPOSITION

FIELD OF THE INVENTION

The present invention relates to a hair conditioning composition.

BACKGROUND OF THE INVENTION

Hair damages are caused by environments (ultraviolet and heat due to sunlight, drying), daily hair care behavior (shampooing, brushing, and heat from a dryer), and chemical treatments (coloring, perm, and the like). Thus, various hair rinses and hair conditioners have been developed in order to repair damaged hairs which have increased friction and whose surfaces are unoiled, thereby enabling the damaged hairs to regain their smooth touch.

Patent Document 1, aimed at obtaining better spread and suppleness when applied on the hair, discloses a hair rinse agent composition containing a cationic group-containing polymer and polyoxyethylene polyoxypropylene alkyl ether, polyoxypropylene alkyl ether, or a mixture of polyoxyethylene polyoxypropylene alkyl ether and polyoxypropylene alkyl ether.

Patent Document 2, aimed at obtaining hair cosmetics which increase a hair styling force, giving moisture to the hair, and making the hair moist and supple and not greasy, discloses a hair cosmetic containing a polyoxyalkylene-based compound obtained by addition-polymerization of an alkylene oxide and a monovalent or polyvalent alcohol, and a crosslinking type polyacrylic acid polymer.

Patent Document 3, aimed at imparting good feels to the damaged hair without greasy and oily feelings, discloses a hair cosmetic containing alkyl polyalkylene glycol ethers, a cationic surfactant, and a fatty acid having an alkyl group having 12 to 40 carbon atoms.

Patent Document 4 discloses a cosmetic composition containing (a) a mixture of nonionic surfactants selected from straight or branched oxyethylenated and/or oxypropylenated and/or polyglycerolized fatty alcohols at a ratio of 14 to 50%, with the mixture containing at least one surfactant A having an HLB value, as a value used by Griffin, which is not lower than 14, and a nonionic surfactant B having an HLB value, as a value used by Griffin, which is not lower than 1 and is lower than 10 at a specific rate, and containing (b) a cationic or amphoteric substantive polymer at a ratio of 0.05 to 10%, as compositions used for staining keratin fibers and producing bleach compositions.

However, these conventional technologies are so problematic that even if hair manageability has been increased, that is, hair looseness has been prevented, greasy feel is inevitably caused thereby. On the other hand, even if greasy feel has been prevented, hair manageability is insufficient. Thus, it has been impossible to satisfy both of hair manageability and a moisturized feel with no greasy feel.

[Patent Document 1] JP-A-62-132812
[Patent Document 2] JP-A-01-106812
[Patent Document 3] JP-A-04-230614
[Patent Document 4] JP-A-07-267836

SUMMARY OF THE INVENTION

The present invention provides a hair conditioning composition containing the following components (A) and (B):
(A) a compound represented by a general formula (1)

$$R^1O-(PO)_n/(EO)_m-R^2 \tag{1}$$

where $R^1$ represents a straight or branched, alkyl or alkenyl group having 8 to 12 carbon atoms, PO represents a propyleneoxy group, EO represents an ethyleneoxy group, an average addition mole number "n" represents a number of 1.5 to 3.0, an average addition mole number "m" represents a number of 0 to 1.0, and $R^2$ represents a hydrogen atom or a methyl group; and
(B) a surfactant other than the component (A),
wherein a content of $R^1OH$ (where $R^1$ represents a straight or branched, alkyl or alkenyl group having 8 to 12 carbon atoms) is 80 ppm or less.

The present invention also provides a hair conditioning composition containing the above components (A) and (B), and a component (C) being an oily component, wherein a content of $R^1OH$ (where $R^1$ represents a straight or branched, alkyl or alkenyl group having 8 to 12 carbon atoms) is 80 ppm or less.

The present invention also provides use of a composition, as a hair conditioning agent, containing the above components (A) and (B), wherein a content of $R^1OH$ (where $R^1$ represents a straight or branched, alkyl or alkenyl group having 8 to 12 carbon atoms) is 80 ppm or less.

The present invention also provides use of a composition, as a hair conditioning agent, containing the above components (A), (B), and (C), wherein a content of $R^1OH$ (where $R^1$ represents a straight or branched, alkyl or alkenyl group having 8 to 12 carbon atoms) is 80 ppm or less.

The present invention also provides a method of conditioning the hair, which includes using, for the hair, the composition containing the above components (A) and (B), wherein a content of $R^1OH$ (wherein $R^1$ represents a straight or branched, alkyl or alkenyl group having 8 to 12 carbon atoms) is 80 ppm or less.

The present invention provides a method of conditioning the hair, which includes using, for the hair, the composition containing the above components (A), (B), and (C), wherein a content of $R^1OH$ (where $R^1$ represents a straight or branched, alkyl or alkenyl group having 8 to 12 carbon atoms) is 80 ppm or less.

DETAILED DESCRIPTION OF THE INVENTION

The present invention is to provide a hair conditioning composition which is excellent in oily feel (low greasy feel) by hand transfer upon finish, and can impart good manageability and moisturized feel.

According to the present invention, there is obtained a low odor hair conditioning composition which is excellent in oily feel (low greasy feel) by the hand transfer upon finish, and can impart the good manageability and the moisturized feel.

According to the present invention, it has been found that a hair conditioning composition containing polyoxyethylene polyoxypropylene alkyl ether having a relatively short chain alkyl group and having low addition mole numbers of ethyleneoxy group and propyleneoxy group within a certain range and a surfactant is not oily and greasy upon finish compared with oil solutions generally used, can impart the good manageability and moisturized feel, and further has low odor. Thus the present invention has been completed.

The composition of the present invention containing the above components (A) and (B) is suitable for non-wash-off type hair conditioning compositions, and the composition containing the above components (A), (B), and (C) is suitable for wash-off type hair conditioning compositions.

Hereinafter, constitutions of the present invention are described in detail.

In the general formula (1) of the component (A), $R^1$ represents a straight or branched, alkyl or alkenyl group having 8 to 12 and preferably 8 to 10 carbon atoms, and preferably represents the straight or branched, alkyl group in terms of reducing the odor. In the non-wash-off type having the low odor and hair manageability, $R^1$ preferably represents an alkyl group having 8 carbon atoms, and when $R^1$ represents a mixed alkyl group, an alkyl group having 8 carbon atoms occupies preferably 50 mol % or more, more preferably 80 mol % or more, and even more preferably 98 mol % or more, in terms of oily feel by the hand transfer. When the number of carbon atoms in $R^1$ exceeds 12, the hair conditioning composition is excellent in suppleness to the hair and moisturized feel, but is inferior in hair manageability, and increases the oily feel by the hand transfer. Thus, this is not favorable. When the number is less than 8, the manageability and the moisturized feel are sometimes inferior. When the number of carbon atoms in $R^1$ is 8 to 10, softness to the hair is excellent. It is conceivable that the hair conditioning composition of the present invention is excellent in oily feel by the hand transfer, as well as is excellent in hair manageability and moisturized feel, because the component (A) has both properties of a surfactant and an oily component.

In the general formula (1) of the component (A), PO and EO may be block-polymerized or random-polymerized, but are preferably block-polymerized. In terms of reducing the odor, $(PO)_n/(EO)_m$ is preferably (added) aligned in a block form in an order of $(PO)_n$ and $(EO)_m$ with respect to $R^1O$.

In the compound of the general formula (1) of the component (A), average addition mole numbers "n" and "m" are restricted by the balance of the odor, the moisturized feel, and the hair manageability. That is, when the average addition mole numbers "n" and "m" are small, the content of material alcohol is increased, the odor is increased, as well as the moisturized feel and the hair manageability are impaired. Meanwhile, when the average addition mole numbers "n" and "m" are large, spread upon application is good, but the hair manageability and the oily feel by the hand transfer are inferior. Thus, these are not favorable.

The average addition mole number "n" represents the number of 1.5 to 3.0, preferably 2.0 to 3.0, and more preferably 2.2 to 2.8 in terms of odor, oily feel by the hand transfer, moisturized feel, and hair manageability.

The average addition mole number "m" represents the number of 0 to 1.0, and preferably 0 to 0.5, and more preferably 0 in terms of hair manageability.

The number of "n+m" is preferably 1.5 to 4.0, more preferably 1.5 to 3.0, and even more preferably 2.0 to 2.8 in terms of odor, oily feel by the hand transfer, moisturized feel, and hair manageability.

The average addition mole numbers "n" and "m" in the general formula (1) are the average. Thus, the addition mole numbers in individual molecules have distribution. For the distribution of the addition mole numbers of PO in those mole numbers, the total rate of compounds containing 2 and 3 moles of PO addition mole number based on compounds containing 1 to 5 moles of PO addition mole number contained in the component (A) is preferably 58 to 80 mol % and more preferably 60 to 70 mol % in terms of oily feel by the hand transfer, moisturized feel, and hair manageability.

Further, the rate of a compound containing 1 mole of PO addition mole number is preferably 10 to 25 mol %, the rate of a compound containing 2 moles of PO addition mole number is preferably 34 to 40 mol %, the rate of a compound containing 3 moles of PO addition mole number is preferably 20 to 30 mol %, the rate of a compound containing 4 moles of PO addition mole number is preferably 9 to 18 mol %, and the rate of a compound containing 5 moles of PO addition mole number is preferably 3 to 9 mol %, in the compounds containing 1 to 5 moles of PO addition mole number contained in the component (A), in terms of oily feel by the hand transfer, moisturized feel, hair manageability, and production.

Values of the average addition mole numbers "n" and "m" can be determined by $^1$H-NMR. The distribution of the PO addition mole number can be determined by the gas chromatography described later, and the above values are determined by focusing on a compound containing added PO alone even if EO is added.

$R^2$ in the general formula (1) represents a hydrogen atom or a methyl group, and is preferably a hydrogen atom.

The component (A) is contained in an amount of preferably 0.1 to 10% by weight, more preferably 0.1 to 7% by weight, more preferably 0.3 to 7% by weight, more preferably 0.3 to 5% by weight, more preferably 0.5 to 5% by weight, and even more preferably 1 to 5% by weight in the hair conditioning composition, in terms of oily feel by the hand transfer, moisturized feel, and hair manageability.

A compound represented by $R^1OH$ (where $R^1$ represents a straight or branched, alkyl or alkenyl group having 8 to 12 carbon atoms) in the general formula (1), in which "n" and "m" each represent 0, and $R^2$ represents a hydrogen atom, and preferably, a compound represented by $R^1OH$ (where $R^1$ represents a straight or branched, alkyl or alkenyl group having 8 to 10 carbon atoms) are contained in an amount of preferably 3,000 ppm or less, more preferably 2,000 ppm or less, more preferably 1,500 ppm or less, more preferably 1,000 ppm or less, and even more preferably 500 ppm or less in the component (A), in terms of low odor, moisturized feel, and hair manageability.

The component (A) used in the present invention can be obtained by reacting propylene oxide, or propylene oxide and ethylene oxide with material alcohol represented by $R^1OH$ (where $R^1$ represents a straight or branched, alkyl or alkenyl group having 8 to 12 and preferably 8 to 10 carbon atoms) using a basic catalyst, followed by distilling off the material alcohol. The average addition mole numbers of propylene oxide and ethylene oxide added in the reaction are preferably the values of "n", "m" and "n+m" as described above.

Therefore, $R^1OH$ contained in the component (A) is derived from material alcohol. Thus, when $R^1$ represents 8 to 10 carbon atoms in the general formula (1) of the component (A), $R^1$ in $R^1OH$ contained in the component (A) also represents 8 to 10 carbon atoms.

As the basic catalyst, potassium hydroxide, sodium hydroxide, lithium hydroxide, sodium alkoxide, or the like is used, and they are used in a proportion of preferably 0.1 to 5 mol % and more preferably 0.1 to 2 mol % with respect to material alcohol represented by $R^1OH$. The reaction temperature is preferably 80 to 200° C. and more preferably 110 to 160° C. The reaction pressure is preferably 0.1 to 0.8 MPa and more preferably 0.1 to 0.6 MPa.

A reaction product can be directly subjected to distillation, but can also be subjected to distillation off after removing the basic catalyst with a neutralizing agent, or an adsorbing agent, or the like. The distillation off of material alcohol means that the material alcohol is distilled off by the distillation or a water vapor treatment, or by combining the distillation and the water vapor treatment. The water vapor treatment means that the water vapor is blown into a reaction composition and the material alcohol together with the water vapor is removed out of a system. A preferable condition for the removal is as follows.

Temperature: 80 to 200° C., preferably 80 to 150° C.

Pressure: 27 kPa (200 torr) or less, preferably 6 kPa (45 torr) or less.

Amount of water vapor: 0 to 50 parts by weight with respect to 100 parts by weight of reaction composition.

The hair conditioning composition of the present invention contains a surfactant (B) in terms of stably including the component (A) and uniformly applying it.

The surfactants of the component (B) are one or more surfactants selected from the group consisting of anionic surfactants, nonionic surfactants other than the component (A), amphoteric surfactants, and cationic surfactants, and are preferably the nonionic surfactants and the cationic surfactants, and more preferably the cationic surfactants.

The cationic surfactants are preferably quaternary ammonium salt type cationic surfactants or tertiary amine type cationic surfactants. The quaternary ammonium salt type cationic surfactants are preferably those represented by the general formula (2), and the tertiary amine type cationic surfactants are preferably those represented by the general formula (3).

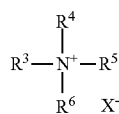

(2)

In the formula, one or two of $R^3$, $R^4$, $R^5$, and $R^6$ each represent a hydrocarbon group or an aliphatic acyloxy (polyethoxy) ethyl group having 8 to 35 total carbon atoms, which may be interrupted with a functional group represented by —O—, —CONH—, —NHCO—, —OCO—, or —COO—, or may be substituted with —OH and the remainders each independently represent an alkyl or a hydroxyalkyl group having 1 to 4 carbon atoms or a polyoxyethylene group, and X represents a halide ion or an organic anion.

(3)

In the formula, one of $R^7$ to $R^9$ represents a hydrocarbon group having 8 to 35 total carbon atoms, which may be interrupted with a functional group represented by —O—, —CONH—, —NHCO—, —OCO—, or —COO—, or may be substituted with —OH and the remainders each independently represent an alkyl group having 1 to 4 carbon atoms.

The hydrocarbon group represented by one or two of $R^3$, $R^4$, $R^5$, and $R^6$ in the general formula (2) is a straight or branched, saturated or unsaturated hydrocarbon group having 8 to 35, preferably 12 to 28, and more preferably 12 to 25 total carbon atoms. The hydrocarbon group may be interrupted with a functional group represented by —O— (oxy group), —CONH— (amide group), —NHCO— (carbamoyl group), —OCO— (oxycarbonyl group), or —COO— (acyloxy group). The hydrocarbon group may have —OH (hydroxyl group) as a substituent.

As an alkyl group or a hydroxyalkyl group having 1 to 4 carbon atoms, or a polyoxyethylene group, a methyl group, an ethyl group, a propyl group, an isopropyl group, a butyl group, a t-butyl group, a hydroxyethyl group, and a hydroxypropyl group or the like are exemplified. Of those, a methyl group and an ethyl group are preferred, and a methyl group is more preferred. A polyoxyethylene group having a total addition mole number of 10 or lower is preferably exemplified.

Specific examples of $X^-$ include halogen ions such as $Cl^-$ and $Br^-$, alkyl sulfate ions having 1 to 5 carbon atoms (such as $CH_3SO_4^-$, $C_2H_5SO_4^-$, and $C_3H_7SO_4^-$), and an alkyl carbonate ion ($CH_3CO_3^-$), and $Cl^-$, $Br^-$, $CH_3SO_4^-$, $C_2H_5SO_4^-$, and $CH_3CO_3^-$ are preferred. As an aliphatic acyloxy(polyethoxy) ethyl group, an acyl group having 8 to 22 carbon atoms is preferred, and the average addition mole number of a polyethoxy group is 0 to 5 though the polyethoxy group may be or may not be included in the acyl group.

Examples of the quaternary ammonium salt-type cationic surfactants represented by the general formula (2) include mono-long-chain alkyl (having 12 to 28 carbon atoms) quaternary ammonium salts, di-long-chain alkyl (having 12 to 28 carbon atoms) quaternary ammonium salts, branched-chain alkyl (having 12 to 28 carbon atoms) quaternary ammonium salts, alkylamido (having 12 to 28 carbon atoms) alkyl (having 1 to 5 carbon atoms) quaternary ammonium salts, N-hydrocarbon (having 12 to 28 carbon atoms) carbamoyl alkyl (having 1 to 5 carbon atoms) quaternary ammonium salts, acyl (having 12 to 28 carbon atoms) oxyalkyl (having 1 to 5 carbon atoms) quaternary ammonium salts, and alkyl or alkenyl (having 12 to 28 carbon atoms) oxyalkyl (having 1 to 5 carbon atoms) quaternary ammonium salts.

Examples of the mono-long-chain alkyl (having 12 to 28 carbon atoms) quaternary ammonium salts include stearyltrimethyl ammonium chloride, myristyltrimethyl ammonium chloride, cetyltrimethyl ammonium chloride, arachyl trimethyl ammonium chloride, behenyl trimethyl ammonium chloride, lauryl trimethyl ammonium chloride, N-stearyl-N,N,N-tri(polyoxyethylene)ammonium chloride (total addition mole number: 3 moles) or the like.

Examples of the di-long-chain alkyl or alkenyl (having 12 to 28 carbon atoms) quaternary ammonium salts include distearyl dimethyl ammonium chloride, dioleyl dimethyl ammonium chloride, dipalmityl methylhydroxyethyl ammonium methosulfate, diisostearyl dimethyl ammonium methosulfate, di[(2-dodecanoylamino)ethyl]dimethyl ammonium chloride, and di[2-stearoylamino)propyl]dimethyl ammonium sulfate or the like.

Examples of the branched-chain alkyl (having 12 to 28 carbon atoms) quaternary ammonium salts include 2-decyltetradecyl trimethyl ammonium chloride, 2-dodecylhexadecyl trimethyl ammonium chloride, di-2-hexyldecyl dimethyl ammonium chloride, and di-2-octyldodecyl dimethyl ammonium chloride or the like.

Examples of the alkylamido (having 12 to 28 carbon atoms) alkyl (having 1 to 5 carbon atoms) quaternary ammonium salts include stearamidopropyl quaternary ammonium salts. Examples of the N-hydrocarbon (having 12 to 28 carbon atoms) carbamoyl alkyl (having 1 to 5 carbon atoms) quaternary ammonium salts include N-stearylcarbamoyl propyl quaternary ammonium salts. Examples of the acyl (having 12 to 28 carbon atoms) oxyalkyl (having 1 to 5 carbon atoms) quaternary ammonium salts include stearoylpropyl quaternary ammonium salts. Examples of the hydrocarbon (having 12 to 28 carbon atoms) oxyalkyl (having 1 to 5 carbon atoms) quaternary ammonium salts include octadecyloxypropyl trimethyl ammonium chloride or the like.

One of $R^7$ to $R^9$ in the general formula (3) represents a straight or branched, saturated or unsaturated hydrocarbon group having 8 to 35, preferably 12 to 28, and more preferably 12 to 25 total carbon atoms. The hydrocarbon group may be interrupted with a functional group represented by —O—, —CONH—, —NHCO—, —OCO—, or —COO—, or may be substituted with —OH. The remainders each independently represent an alkyl group having 1 to 4 carbon atoms.

Examples of the alkyl group having 1 to 4 carbon atoms include a methyl group, an ethyl group, a propyl group, an isopropyl propyl, a butyl group, and a t-butyl group or the like. Of those, preferred are a methyl group and an ethyl group, and more preferred is a methyl group.

Specific examples of the tertiary amine-type compound preferably include N,N-dimethyloctadecyloxypropyl amine and stearamidopropyldimethyl amine or the like.

As the tertiary amine type cationic surfactant, a tertiary amine compound represented by the general formula (3) may be used directly, or an acid addition salt thereof maybe used. As an acid, an inorganic acid or an organic acid is used.

Examples of the nonionic surfactant include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers other than the component (A), polyoxyalkylene alkyl phenyl ethers, polyoxyalkylene (hardened) castor oils, sucrose fatty acid esters, polyglycerol alkyl ethers, polyglycerol fatty acid esters, and alkyl glycosides or the like. Of those, preferred are alkyl glycosides, polyoxyethylene ($C_8$ to $C_{20}$) alkyl ethers (preferably having an average addition mole number of EO of 3 to 50), polyoxyethylene sorbitan fatty acid ester, polyoxyethylene hardened castor oil, and fatty acid alkanol amide.

As the surfactant, an anionic surfactant or an amphoteric surfactant can also be used without impairing the effects of the present invention.

Examples of the anionic surfactant preferably include sulfuric acid-based surfactants, sulfonic acid-based surfactants, carboxylic acid-based surfactants, phosphoric acid-based surfactants, and amino acid-based surfactants. Specific examples of the anionic surfactant include alkyl sulfates, polyoxyalkylene alkyl ether sulfates, polyoxyalkylene alkenyl ether sulfates, salts of sulfosuccinic acid alkyl esters, salts of polyoxyalkylene sulfosuccinic acid alkyl esters, polyoxyalkylene alkyl phenyl ether sulfates, alkanesulfonates, acyl isethionate, acyl methyl taurate, higher fatty acid salts, polyoxyalkylene alkyl ether acetates, alkyl phosphate, polyoxyalkylene alkyl ether phosphates, acyl glutamate, alanine derivatives, glycine derivatives, and arginine derivatives or the like.

Examples of the amphoteric surfactant include betaine-based surfactants and amine oxide-type surfactants or the like. Of those, more preferred are betaine-based surfactants such as imidazoline-based betaines, alkyldimethylaminoacetic acid betaines, fatty acid amide propyl betaines, and sulfobetaines, and amine oxide-type surfactants such as alkyl dimethyl amine oxide. Even more preferred are sulfobetaines such as alkylcarboxymethylhydroxyethyl imidazolium betaines, fatty acid amide propyl betaines, alkyl hydroxy sulfobetaines, alkyl sulfobetaines, fatty acid amide propyl hydroxy sulfobetaines, and fatty acid amide propyl sulfobetaines, and alkyl dimethyl amine oxide.

Two or more surfactants can be used in combination, and the content of a surfactant is preferably 0.1 to 10% by weight, more preferably 0.3 to 7% by weight, and even more preferably 0.3 to 5% by weight in the hair conditioning composition in terms of stability and feel.

A weight ratio of the component (A) to the surfactant (B) [(A)/(B)] is preferably 1/5 to 5/1, more preferably 1/5 to 3/1, even more preferably 1/3 to 3/1 in terms of oily feel by the hand transfer, moisturized feel, and hair manageability.

The composition of the present invention preferably contains an oily component (C) in the case of the wash-off type in order to stably include the component (A) and enhance the manageability and the moisturized feel while restraining the hand transfer by an interaction with the component (A) and the component (C).

The oily component includes a higher alcohol, silicone, and an ester oil, hydrocarbons, glycerides, vegetable oils, animal oils, lanoline derivatives, and higher fatty acid esters or the like, and from the above viewpoint, are preferably a higher alcohol, an ester oil, and/or silicone, more preferably a higher alcohol and/or silicone, and even more preferably a higher alcohol.

Examples of the higher alcohol include: higher alcohols containing a straight or branched, alkyl or alkenyl group; preferably higher alcohols containing a straight or branched, alkyl or alkenyl group having 16 to 26 carbon atoms and more preferably higher alcohols containing a straight or branched, alkyl or alkenyl group having 16 to 22 carbon atoms; more preferably higher alcohols such as cetanol, cetyl alcohol, stearyl alcohol, arachyl alcohol, behenyl alcohol, carnaubyl alcohol, ceryl alcohol, oleyl alcohol, and isostearyl alcohol; and even more preferably a mixture of one or two or more of cetanol, cetyl alcohol, stearyl alcohol, and behenyl alcohol. Here, cetanol refers to an alcohol containing cetyl alcohol as a main component and also containing higher alcohols such as stearyl alcohol and oleyl alcohol.

The ester oil is preferably a monoester oil, or a mixture of one or two or more ester oils having two or more ester bonds in their molecule.

Examples of the monoester oils include monoester oils having 8 to 40 carbon atoms in total, preferably monoesters of a monovalent fatty acid having 2 to 22 carbon atoms and a monohydric or polyhydric alcohol having 1 to 20 carbon atoms, and more preferably monoesters of a monovalent fatty acid having 8 to 20 carbon atoms and a monohydric or polyhydric alcohol having 1 to 20 carbon atoms or the like, provided that those alcohols may be straight or branched, and saturated or unsaturated. Among them, preferred are isopropyl palmitate, isopropyl myristate, isononyl isononanoate, triisodecyl isononanoate, stearyl stearate, and diglyceryl monoisostearate.

As a polyvalent ester oil having two or more ester bonds in its molecule, exemplified are polyvalent ester oils having 8 to 120 total carbon atoms, and preferably polyvalent esters of a mixture of one or two or more monovalent or polyvalent fatty acids having 2 to 22 carbon atoms and a mixture of one or two or more monohydric or polyhydric alcohols having 2 to 20 carbon atoms. These may be straight or branched, and may be saturated or unsaturated, and further may contain an aromatic ring. Neopentyl glycol dicaprate, diglyceryl diisostearate, or an ester of dipentaerythritol with mixed fatty acids of hydroxystearic acid, stearic acid, and rosin or the like is more preferable.

Examples of the silicones include (a) dimethyl polysiloxane, (b) methyl phenyl polysiloxane, (c) amino-modified silicones [as aqueous emulsions, exemplified are SM8704C (manufactured by Dow Corning Toray Co., Ltd.) and DC939 (manufactured by Dow Corning Toray Co., Ltd.)], (d) fatty acid-modified polysiloxane, (e) alcohol-modified silicones, (f) aliphatic alcohol-modified polysiloxane, (g) polyether-modified silicones, (h) epoxy-modified silicones, (i) fluorine-modified silicones, (j) cyclic silicones, (k) alkyl-modified silicones, and (l) amino-modified siloxane-polyoxyalkylene block copolymers or the like, all of which are described in JP-A-06-48916.

Two or more oily components can be used in combination, and the content of an oily component is preferably 1 to 10% by weight, more preferably 1.5 to 8% by weight, and even more preferably 2 to 5% by weight in the hair conditioning composition of the present invention, in terms of imparting good finger combing and smoothness to wet hairs, moist feel after drying, and emulsification stability.

The weight ratio of the component (A) to the component (C) (oily component) [(A)/(C)] in the wash-off type is preferably 1/5 to 5/1, more preferably 1/5 to 3/1, more preferably 1/4 to 2/1, and even more preferably 1/3 to 1 in terms of enhancing the oily feel by the hand transfer, the moisturized feel, and the hair manageability, and the weight ratio in the non-wash-off type is preferably 10/1 to 1/1 and more preferably 10/1 to 5/1 in terms of enhancing the oily feel by the hand transfer, the moisturized feel, and the hair manageability.

The weight ratio of the component (B) (surfactant) to the component (C) (oily component) [(B)/(C)] is preferably 1/10 to 2/1, more preferably 1/7 to 3/2, and even more preferably 1/5 to 1/1 in terms of stability of the oily component, oily feel by the hand transfer, and hair manageability.

The composition of the present invention preferably further contains a component (D), naphthalene sulfonic acid, oxybenzone sulfonic acid, or salts thereof in terms of enhancing the hair manageability.

The salts thereof include alkali metal salts such as sodium salts and potassium salts, alkali earth metal salts such as calcium salts and magnesium salts, and organic salts such as ammonium and alkanol ammonium. Of those, 2-naphthalene sulfonic acid or a salt thereof is preferable.

Two or more components (D) may be used in combination, and the content of a component (D) is preferably 0.05 to 5% by weight, more preferably 0.1 to 3% by weight, and even more preferably 0.3 to 1.5% by weight in the hair conditioning composition of the present invention, in terms of enhancing the hair manageability. The weight ratio of the component (D) to the component (A) [(D)/(A)] is preferably 1/5 to 3/1, more preferably 1/4 to 2.5/1, and even more preferably 1/3 to 2/1 in terms of hair manageability and moisturized feel.

Further, a thickening polymer can be included in the hair conditioning composition of the present invention. The thickening polymer includes hydroxyethylcellulose, guar gum, xanthan gum, and a polyacrylic acid-based polymer. The content of the thickening polymer is preferably 0.01 to 20% by weight and more preferably 0.05 to 15% by weight in the conditioning composition.

In the hair conditioning composition of the present invention, the content of water varies depending on the form in which the composition is used and is preferably 70 to 97% by weight and more preferably 80 to 95% by weight in the wash-off type, and the content of the water is preferably 80 to 99% by weight and more preferably 85 to 98% by weight in the non-wash-off type.

Products obtained by hydrolyzing proteins and typified by water-soluble collagen and collagen derivatives, which are publicly known components included in a hair conditioning agent, can also be further included in the hair conditioning composition of the present invention. Chelating agents, coloring agents, preservatives, pH adjusters, viscosity adjusters, perfumes, pearl brighteners, and wetting agents or the like may also be included.

The hair conditioning composition of the present invention, which is the wash-off type, is preferably used for a hair conditioning composition such as a hair rinse, a hair treatment agent, and a hair conditioner, and is preferably used for a method in which after washing hair with a shampoo, an appropriate amount of the composition of the present invention is applied to the hair and well dispersed in the hair, followed by being washed off using water or warm water.

The hair conditioning composition of the present invention, which is the wash-off type, can be used in various forms such as a liquid form, an emulsion form, a cream form, a gel form, and a mousse form, and is used preferably in the form of an emulsified composition.

In the emulsified composition, the number of the carbon atoms in $R^1$ in the component (A) is preferably 8 to 10 in order to allow the component (A) to work as an oil solution in terms of enhancing a conditioning performance.

The hair conditioning composition of the present invention, which is the non-wash-off type, can be used as a conditioner (leave-on conditioner), a hair cream, a blow lotion, a hair pack, a conditioning gel, and a conditioning foam or the like, which are the non-wash-off types.

The composition of this type is preferably used by applying an appropriate amount of the composition of the present invention to the hair and dispersing it in the hair after washing the hair with the shampoo.

The hair conditioning composition which is the non-wash-off type can be used in various forms such as a liquid form, an emulsion form, a cream form, a gel form, and a mousse form.

A more preferable aspect of the present invention is, in terms of enhancing the oily feel by the hand transfer, the moisturized feel, the hair manageability, and hair softness, a hair conditioning composition containing the following components (A') and (B') [and further (C') in the wash-off type], in which the content of $R^1OH$ (where $R^1$ represents a straight or branched, alkyl or alkenyl group having 8 to 10 carbon atoms) is 80 ppm or less, and the wash-off type is preferably an emulsified composition:

a component (A'): a compound represented by a general formula (1'):

$$R^1O\text{—}(PO)_n/(EO)_m\text{—}R^2 \tag{1'}$$

where $R^1$ represents a straight or branched, alkyl or alkenyl group having 8 to 10 carbon atoms, PO represents a propyleneoxy group, EO represents an ethyleneoxy group, an average addition mole number "n" represents a number of 1.5 to 3.0, an average addition mole number "m" represents a number of 0 to 1.0, and $R^2$ represents a hydrogen atom or a methyl group;

a component (B'): a surfactant, preferably, a cationic surfactant; and a component (C'): a higher alcohol having 16 to 26 carbon atoms, wherein the emulsified composition is preferably an oil-in-water type (OW).

The hair conditioning composition of the present invention can be produced by a standard method. For example, the component (B) and the component (A) can be mixed, and stirred if necessary with heating to make a dispersed state or a solubilized state. When the component (C) is included, the component (A) together with the component (C) may be added to a mixture of the component (B) and water under being heated to make an emulsified product, or the component (C) may be added to the mixture of the component (B) and the water under being heated to make an emulsified product and then after cooling the emulsified product, the component (A) may be added thereto. Alternatively, the component (A) can also be dispersed or solubilized with the component (B).

In the hair conditioning composition of the present invention, a pH value (20° C.) is preferably 2 to 7 and more preferably 2.5 to 5 in terms of hair manageability.

In the hair conditioning composition of the present invention, the content of a compound represented by $R^1OH$ (where $R^1$ represents a straight or branched, alkyl or alkenyl group having 8 to 12 carbon atoms) in the general formula (1) where "n" and "m" each represent 0 and $R^2$ is a hydrogen atom, preferably a compound represented by $R^1OH$ (where $R^1$ represents a straight or branched, alkyl or alkenyl group having 8 to 10 carbon atoms) is preferably 80 ppm or less, more preferably 50 ppm or less, and even more preferably 30 ppm or less in terms of reducing the odor and in terms of moisturized feel and hair manageability. The lower limit of the content is not particularly limited, and the content is preferably 1 ppm or more in terms of easiness in the production.

$R^1OH$ contained in the hair conditioning composition of the present invention is derived from $R^1OH$ contained in the component (A). Thus, when $R^1$ in the general formula (1) of the component (A) has 8 to 10 carbon atoms, $R^1$ of $R^1OH$ contained in the hair conditioning composition also has 8 to 10 carbon atoms. Therefore, to make the content of $R^1OH$ 80 ppm or less in the conditioning composition of the present invention, material alcohol in the component (A) is preferably distilled off to reduce the content of the material alcohol.

In order to make the content of $R^1OH$ within the above ranges, the component (A) containing a low amount of $R^1OH$ as described above may be used, or the material alcohol for $R^1OH$ can also be removed after blending the component (A), but $R^1OH$ can be reduced more efficiently in the former way.

EXAMPLES

The present invention is described in more detail with reference to the following examples, but the present invention is not limited thereto.

Production Example 1

1-Octanol (Kalcol 0898 manufactured by Kao Corporation) (1,615.0 g, 12.35 mol) and potassium hydroxide (6.9 g, 0.12 mol) were placed in an autoclave, and dehydrated at 110° C. and 13.3 kPa. Subsequently, an addition reaction was performed while propylene oxide (1,434 g, 24.69 mol) was added with a pressure of 0.3 MPa at 120° C.

After terminating the reaction, maturation was performed at the same reaction temperature for 6 hours, and then the resultant was cooled to a temperature of 80° C. As an after-treatment, 55 g of a synthetic adsorbing agent (Kyoward 600S manufactured by Kyowa Chemical Industry Co., Ltd.) was added to the resulting reacted composition, and treatment was performed at 4.0 kPa for 1 hour followed by removing the catalyst by filtration. The content of 1-octanol in the obtained filtrate was 9,000 ppm as a result of quantifying by gas chromatography.

Then, in 1,000 g of the obtained filtrate, 1-octanol was distilled off by distillation under a condition of at 130° C. and 1.3 kPa. A water vapor treatment was further performed by blowing 100 g of water vapor under a condition of at 145° C. and 6.0 kPa for 5 hours.

The content of 1-octanol in the resulting component (A) (alkylene glycol ether 1 shown in Table 1) was quantified by gas chromatography.

Condition of gas chromatography
Gas chromatograph: Agilent Technologies, HP6890N
Column: Frontier LAB, Ultara-Alloy-1
Temperature condition: Initial temperature 100° C. (0 minute)
Rate of temperature increase: 10° C./minute (up to 350° C.)
Final temperature: 350° C. (20 minutes)
Sample amount: 1 μL
Inlet condition: Injection mode, split method
Inlet temperature: 300° C.
Carrier gas: Helium, flow rate, 60 mL/minute
Detector: FID A distribution of addition mole numbers of PO in the component (A) before the distillation and after the distillation and the water vapor treatment was obtained by gas chromatography.

Distribution of PO 1 to 5 of alkylene glycol ether 1 before distillation (molar ratio)
Addition mole number of PO 1: 35.6
Addition mole number of PO 2: 34.9
Addition mole number of PO 3: 18.7
Addition mole number of PO 4: 7.8
Addition mole number of PO 5: 3.0

Distribution of PO 1 to 5 of alkylene glycol ether 1 in component (A) after distillation and water vapor treatment (molar ratio)
Addition mole number of PO 1: 24.6
Addition mole number of PO 2: 39.8
Addition mole number of PO 3: 22.4
Addition mole number of PO 4: 9.5
Addition mole number of PO 5: 3.7

Production Example 7

1-Octanol (Kalcol 0898 manufactured by Kao Corporation) (131.00 g, 1.0 mol) and potassium hydroxide (1.17 g, 0.01 mol) were placed in an autoclave, and dehydrated at 110° C. and 13.3 kPa. Subsequently, an addition reaction was performed while propylene oxide (151.01 g, 2.6 mol) was added with a pressure of 0.3 MPa at 120° C.

After terminating the reaction, maturation was performed at the same reaction temperature for 6 hours, and then the resultant was cooled to a temperature of 80° C. As an after-treatment, 55 g of a synthetic adsorbing agent (Kyoward 600S manufactured by Kyowa Chemical Industry Co., Ltd.) was added to the resulting reacted composition, and treatment was performed at 4.0 kPa for 1 hour, followed by removing the catalyst by filtration. The content of 1-octanol in the obtained filtrate was 5,000 ppm as a result of quantifying by gas chromatography.

Then, in 100 g of the obtained filtrate, 1-octanol was distilled off by distillation under a condition of at 130° C. and 1.3 kPa. A water vapor treatment was further performed by blowing 15 g of the water vapor under a condition of at 145° C. and 6.0 kPa for 5 hours.

The content of 1-octanol in the resulting component (A) (alkylene glycol ether 7 shown in Table 1) was quantified by gas chromatography.

Distribution of PO 1 to 5 of alkylene glycol ether 7 before distillation (molar ratio)
Addition mole number of PO 1: 21.8
Addition mole number of PO 2: 32.0
Addition mole number of PO 3: 24.7
Addition mole number of PO 4: 14.2
Addition mole number of PO 5: 7.3

Distribution of PO 1 to 5 of alkylene glycol ether 7 in component (A) after distillation and steam treatment (molar ratio)
Addition mole number of PO 1: 10.9
Addition mole number of PO 2: 34.9
Addition mole number of PO 3: 28.9
Addition mole number of PO 4: 16.7
Addition mole number of PO 5: 8.6

Production Examples 2 to 6 and 8 to 17

Alkylene glycol ethers 2 to 6 and 8 to 17 shown in Table 1 were obtained in the same way as in Production Example 1, except the following. For alkylene glycol ethers 2 to 6, 8 to 12, 14, 16, and 17, treatment with an adsorbing agent was performed in the same way as in Production Example 1, and subsequently purification by the distillation and the water vapor treatment was performed by adjusting the degree of reduced pressure (pressure) or a period of time to attain the amounts of material alcohol shown in Table 1. For alkylene glycol ethers 13 and 15, only the treatment with an adsorbing agent was performed, and no distillation was performed. The amount of material alcohol in yielded alkylene glycol ether was quantified by gas chromatography.

The average addition mole numbers "n" of PO and "m" of EO in alkylene glycol ether obtained in Table 1 were calculated by $^1$H-NMR.

TABLE 1

| Production Example | | General Formula (1) | | | | Amount of material alcohol (ppm) |
|---|---|---|---|---|---|---|
| | | R1 | R2 | n | m | n = m = 0 |
| 1 | Alkylene glycol ether 1 | C8 | H | 2.4 | 0 | 400 |
| 2 | Alkylene glycol ether 2 | C8 | H | 1.6 | 0 | 1,500 |
| 3 | Alkylene glycol ether 3 | C8/C10 (Molar ratio: 1/1) | H | 3 | 0 | 900 |
| 4 | Alkylene glycol ether 4* | C8 | H | 2 | 0.5 | 500 |
| 5 | Alkylene glycol ether 5 | C12 | H | 2.7 | 0 | 400 |
| 6 | Alkylene glycol ether 6 | 2-ethylhexyl | H | 3 | 0 | 400 |
| 7 | Alkylene glycol ether 7 | C8 | H | 2.7 | 0 | 400 |
| 8 | Alkylene glycol ether 8 | C12 | H | 2.7 | 0 | 27,000 |
| 9 | Alkylene glycol ether 9 | C8 | H | 6 | 0 | 400 |
| 10 | Alkylene glycol ether 10 | C8 | H | 6 | 0 | 26,000 |
| 11 | Alkylene glycol ether 11 | C8 | H | 0 | 2 | 30,000 |
| 12 | Alkylene glycol ether 12 | C8/C18 (Molar ratio: 1/1) | H | 0 | 9 | 5,000 |
| 13 | Alkylene glycol ether 13 | C8 | H | 0 | 3 | 190,000 |
| 14 | Alkylene glycol ether 14 | C12 | H | 0 | 6 | 50,000 |
| 15 | Alkylene glycol ether 15 | 2-ethylhexyl | H | 0 | 4 | 150,000 |
| 16 | Alkylene glycol ether 16 | C6 | H | 3 | 0 | 26,000 |
| 17 | Alkylene glycol ether 17 | C12 | H | 3 | 0 | 27,000 |
| | Alkylene glycol ether 18** | C3 (Propyl) | H | 2 | 0 | — |

*(PO)n and (EO)m are aligned for R1 in a block form in the order of (PO)n and (EO)m.
**Dipropylene glycol monopropyl ether manufactured by Wako Pure Chemical Industries Ltd.

Examples 1 to 12, Comparative Examples 1 to 11

Hair conditioning compositions each having a composition shown in Tables 2 and 3 were prepared by the following production method, applied to hair, dried, and subsequently evaluated for the feel of finish (hair manageability, hand transfer feel of oil, and moisturized feel) and the odor of the compositions.

A mixture of the component (A), the component (B), methylparaben, and water in an appropriate amount was stirred until the mixture became clear. Subsequently, when the component (C) was employed, the component (C) was added and stirred. Cosmetics in Comparative Examples 7 to 9 did not become clear and were in a dispersed state.

Evaluation results are also shown in Tables 2 and 3, and % in Tables 2 and 3 denotes % by weight.

[Evaluation Test of Hair Conditioning Compositions]

Evaluation methods and evaluation criteria are shown below.

For evaluating flexibility of the hair, the hair manageability, and the moisturized feel, tresses for a test were used, and a sensory evaluation was performed by panelists. That is, black straight hair from an adult female, having no history of a chemical treatment and having a length of about 40 cm, was used as a specimen. This hair specimen was washed by immersing it in an aqueous solution of sodium lauryl sulfate (2.5% by weight) at 40 to 50° C. for 10 minutes, then washed with running water, and subsequently dried with air. The tress for a test was prepared by aligning the hair specimen (about 4 g) to a width of 3 cm to make a uniform thickness, and fixing its one end on a plastic plate having a width of 3 cm with an adhesive so that the length of the hair was 35 cm. The tress for a test prepared in this way was used.

Graders and Hair Bundles

The sensory evaluation for the feel of the above parameters was performed by three panelists each using the above tress and the criteria shown below.

Manipulation

A hair bundle was sufficiently wetted with warm water at 35 to 40° C., and then washed with a plane shampoo having the following composition. After sufficiently rinsing with warm water, the hair bundle was lightly squeezed to remove extra water, and 1 g of a hair conditioning composition was applied. Each parameter upon application was evaluated, and then the hair bundle was combed. Subsequently, the hair bundle was dried by warm wind from a dryer and combed for the finish, and each parameter upon finish was evaluated.

| Plain shampoo | |
|---|---|
| | (% by weight) |
| Sodium polyoxyethylene laurylether sulfate (EMAL E-27C) (pure content: 27%) | 42 |

-continued

| Plain shampoo | |
|---|---|
| | (% by weight) |
| Coconut oil fatty acid N-methylethanol amide (AMINON C-11S) | 3 |
| Citric acid | 0.2 |
| methylparaben | 0.3 |
| Purified water | balance |
| Total | 100 |

Hair Manageability (Evaluated Visually)
Evaluation Criteria
5; The hair is managed well with no loose hair.
4; The hair is managed well with almost no loose hair.
3; The hair is less managed with some loose hairs.
2; The hair is not managed with loose hairs.
1; The hair is not managed with many loose hairs.
 A score was obtained by averaging the evaluation results by the three panelists.
Moisturized Feel (Evaluated Visually and by Touching Hair with Hands)
Evaluation Criteria
5; When touched, the hair is moist and shiny like wet.
4; When touched, the hair is moderately moist and moderately shiny.
3; When touched, the hair is slightly moist and slightly shiny.
2; When touched, the hair is hardly moist and hardly shiny.
1; When touched, the hair is not moist and shiny.
 A score was obtained by averaging the evaluation results by the three panelists.
Oily Feel by Hand Transfer (Evaluated by Touching Hair with Hands.)
Evaluation Criteria
5; There is no greasy feel.
4; There is almost no greasy feel.
3; There is slightly the greasy feel.
2; There is the greasy feel.
1; There is clearly the greasy feel.
 A score was obtained by averaging the evaluation results by the three panelists.
Odor
4; No odor is recognized.
3; The odor is slightly recognized.
2; The odor is recognized.
1. The odor is strongly recognized.
 A score was obtained by averaging the evaluation results by the three panelists.

TABLE 2

| | | Example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | Raw material name | Pure content % | Pure content % | Pure content % | Pure content % | Pure content % | Pure content % | Pure content % | Pure content % | Pure content % | Pure content % | Pure content % | Pure content % |
| Component (A) | Alkylene glycol ether 1 | 2.0 | | | | | | | | | | | |
| | Alkylene glycol ether 2 | | 2.0 | | | | | | | | | | |
| | Alkylene glycol ether 3 | | | 2.0 | | | | | | | | | |
| | Alkylene glycol ether 4 | | | | 2.0 | | | | | | | | |
| | Alkylene glycol ether 5 | | | | | 2.0 | | | | | | | |
| | Alkylene glycol ether 6 | | | | | | 2.0 | | | | | | |
| | Alkylene glycol ether 7 | | | | | | | 2.0 | 2.0 | 2.0 | 2.0 | 2.0 | 2.0 |
| Component (B) | Emulgen 106 | 5.0 | 5.0 | 5.0 | 5.0 | | 5.0 | 5.0 | 5.0 | 5.0 | | | |
| | Quartamin 60W | | | | | 1.5 | | | | | 1.5 | 1.5 | 1.5 |
| Component (D) | β-NSA | | | | | 1.0 | | | 1.0 | 1.0 | | 1.0 | 1.0 |
| Others | Citric acid | | | | | | | | | | 1.0 | | 1.0 |
| | Methylparaben | 0.3 | 0.3 | 0.3 | 0.3 | 0.3 | 0.3 | 0.3 | 0.3 | 0.3 | 0.3 | 0.3 | 0.3 |
| | Purified water | Balance | Balance | Balance | Balance | Balance | Balance | Balance | Balance | Balance | Balance | Balance | Balance |
| Material alcohol (ppm) | | 8 | 30 | 18 | 10 | 8 | 8 | 8 | 8 | 8 | 8 | 8 | 8 |
| pH | | 6.0 | 6.0 | 6.0 | 6.0 | 6.0 | 6.0 | 6.0 | 6.0 | 3.5 | 6.0 | 6.0 | 3.5 |
| Evaluation | Hair manageability | 4 | 3.8 | 4 | 4 | 4.5 | 4 | 4.3 | 4.7 | 5 | 4.3 | 4.7 | 5 |
| | Moisturized feel | 4 | 4.3 | 4.3 | 4 | 5 | 4.7 | 4.7 | 4.7 | 5 | 5 | 5 | 5 |
| | Oily feel by hand transfer | 4.7 | 4.7 | 4.7 | 4.7 | 5 | 4.7 | 4.7 | 5 | 5 | 4.7 | 5 | 5 |
| | Odor evaluation | 3.7 | 3 | 3 | 3.7 | 3.7 | 4 | 4 | 4 | 4 | 4 | 4 | 4 |

Raw material name
Quartamin 60W: Cetyltrimethyl ammonium chloride (manufactured by Kao Corporation)
Emulgen 106: Lauryl alcohol having 6 moles of average addition mole number of ethylene oxide (manufactured by Kao Corporation)
β-NSA: Sodium 2-naphthalenesulfonate

TABLE 3

| | Raw material name | Comparative Example ||||||||||| 
| | | 1 Pure content % | 2 Pure content % | 3 Pure content % | 4 Pure content % | 5 Pure content % | 6 Pure content % | 7 Pure content % | 8 Pure content % | 9 Pure content % | 10 Pure content % | 11 Pure content % |
|---|---|---|---|---|---|---|---|---|---|---|---|---|
| Component (B) | Emulgen 106 | 5.0 | 5.0 | 5.0 | 5.0 | 5.0 | 5.0 | 5.0 | 5.0 | 5.0 | 5.0 | 5.0 |
| | Alkylene glycol ether 10 | 2.0 | | | | | | | | | | |
| | Alkylene glycol ether 11 | | 2.0 | | | | | | | | | |
| | Alkylene glycol ether 12 | | | 2.0 | | | | | | | | |
| | Alkylene glycol ether 13 | | | | 2.0 | | | | | | | |
| | Alkylene glycol ether 14 | | | | | 2.0 | | | | | | |
| | Alkylene glycol ether 15 | | | | | | 2.0 | | | | | |
| | Alkylene glycol ether 16 | | | | | | | 2.0 | | | | |
| | Alkylene glycol ether 17 | | | | | | | | 2.0 | | | |
| | Octyldodecyl myristate | | | | | | | | | 2.0 | | |
| | Polyglyceryl triisostearate | | | | | | | | | | 2.0 | |
| | Highly polymerized dimethylsiloxane methyl(aminopropyl)siloxane copolymer | | | | | | | | | | | 2.0 |
| | Methylparaben | 0.3 | 0.3 | 0.3 | 0.3 | 0.3 | 0.3 | 0.3 | 0.3 | 0.3 | 0.3 | 0.3 |
| | Purified water | Balance | Balance | Balance | Balance | Balance | Balance | Balance | Balance | Balance | Balance | Balance |
| Material alcohol (ppm) | | 520 | 600 | 100 | 3,800 | 1,000 | 3,000 | 520 | 540 | 0 | 0 | 0 |
| pH | | 6.0 | 6.0 | 6.0 | 6.0 | 6.0 | 6.0 | 6.0 | 6.0 | 6.0 | 6.0 | 6.0 |
| Evaluation | Hair manageability | 2 | 1 | 2 | 2 | 2 | 2 | 2 | 2 | 3.3 | 4 | 4 |
| | Moisturized feel | 2 | 2 | 2 | 1 | 1 | 1 | 1 | 2 | 3.3 | 2 | 2 |
| | Oily feel by hand transfer | 4.7 | 4.7 | 4.7 | 4.7 | 3 | 4.7 | 3 | 4 | 2 | 1 | 2 |
| | Odor evaluation | 1 | 1 | 1.7 | 1 | 1 | 1 | 1 | 1.2 | 4 | 4 | 4 |

Raw material name
Emulgen 106: Lauryl alcohol having 6 moles of average addition mole number of ethylene oxide (manufactured by Kao Corporation)
Polyglyceryl triisostearate: Cosmol 43V (manufactured by Nisshin Oillio Group, Ltd.) Highly polymerized dimethylsiloxane methyl(aminopropyl)siloxane copolymer: KF-8020 (manufactured by Shin-Etsu Chemical Co., Ltd.)

From Tables 2 and 3, there are revealed that the hair conditioning composition of the present invention has the low odor, is excellent in oily feel by the hand transfer upon finish (the greasy feel is low.), and can impart the good hair manageability and moisturized feel. The hair conditioning compositions of the present invention were also excellent in hair softness without impairing a voluminous look of the hair except the composition in Example 5. The hair conditioning composition in Example 5 using alkylene glycol ether 5 containing $R^1$ having 12 carbon atoms was slightly inferior in hair softness.

The hair conditioning composition in Comparative Example 3 using alkylene glycol C18 alkyl ether containing $R^1$ having a large number of carbon atoms was not good in hair manageability and moisturized feel. The hair conditioning compositions in Comparative Examples 2 to 6 using alkylene glycol ether containing a large number of polyoxyethylene molecules had neither the hair manageability nor the moisturized feel. The hair conditioning composition in Comparative Example 1 using alkylene glycol ether containing a large number of polyoxypropylene molecules had neither the hair manageability nor the moisturized feel. The hair conditioning composition in Comparative Example 7 using alkylene glycol ether containing $R^1$ having a small number of carbon atoms lacked both the hair manageability and the moisturized feel and had the strong odor. The hair conditioning compositions in Comparative Examples 9 to 11 were also inferior in a voluminous look of the hair. Further, in the case of using alkylene glycol ether containing a large amount of material alcohol, not only the odor was strong but also the hair manageability and the moisturized feel were inferior.

Examples 13 to 24, Comparative Examples 12 to 27

Hair conditioning compositions (hair rinse) each having a composition shown in Tables 4 and 5 were prepared by the following production method. Hair was rinsed and dried, and each composition was subsequently evaluated for the feel upon finish (hair manageability, hand transfer feel of oil, and moisturized feel) and the odor of the composition.

A mixture of the component (C), an appropriate amount of water, hydroxyethylcellulose, and paraben was heated up to 80° C., and subsequently, a mixture of the component (A) and the component (B) was added to emulsify them, and then, the temperature was cooled to room temperature.

Evaluation results are also shown in Tables 4 and 5. A pure content % in Tables 4 and 5 denotes % by weight.

[Evaluation Test of Hair Conditioning Compositions]

Evaluation methods and evaluation criteria are shown below.

For evaluating flexibility of the hair, the hair manageability, and the moisturized feel, tresses for a test were used, and a sensory evaluation was performed by panelists. That is, black straight hair from an adult female, having no history of a chemical treatment and having a length of about 40 cm, was used as a specimen. This hair specimen was washed by immersing it in an aqueous solution of sodium lauryl sulfate (2.5% by weight) at 40 to 50° C. for 10 minutes, then washed with running water, and subsequently dried with air. The tress for a test was prepared by aligning the hair specimen (about 4 g) to a width of 3 cm to make a uniform thickness, and fixing its one end on a plastic plate having a width of 3 cm with an adhesive so that the length of the hair was 35 cm. The tress for a test prepared in this way was used.

Graders and Hair Bundles

The sensory evaluation for the feel of the above parameters was performed by three panelists each using the above tress and the criteria shown below.

Manipulation

A hair bundle was sufficiently wetted with warm water at 35 to 40° C., and then washed with each of plane shampoos having the above (described in Examples 1 to 12) compositions. After sufficiently rinsing with warm water, the hair bundle was lightly squeezed to remove extra water, and 1 g of a hair conditioning composition was applied. Each parameter upon application described in Examples 1 to 12 was evaluated, and then the hair bundle was combed after the hair bundle was rinsed with warm water, and the water of the bundle was removed with a towel. Subsequently, the hair bundle was dried by warm wind from a dryer and combed for the finish, and each parameter upon finish was evaluated.

TABLE 4

| | | Example | | | | | | | | | | | |
|---|---|---|---|---|---|---|---|---|---|---|---|---|---|
| | | 13 | 14 | 15 | 16 | 17 | 18 | 19 | 20 | 21 | 22 | 23 | 24 |
| | Component name | Pure content % | Pure content % | Pure content % | Pure content % | Pure content % | Pure content % | Pure content % | Pure content % | Pure content % | Pure content % | Pure content % | Pure content % |
| Component (A) | Alkylene glycol ether 1 | 3.0 | | | | | | | 3.0 | | 3.0 | | |
| | Alkylene glycol ether 2 | | 3.0 | | | | | | | 3.0 | 4.5 | | |
| | Alkylene glycol ether 3 | | | 3.0 | | | | | | | | | |
| | Alkylene glycol ether 4 | | | | 3.0 | | | | | | | 3.0 | |
| | Alkylene glycol ether 6 | | | | | 3.0 | | | | | | | |
| | Alkylene glycol ether 7 | | | | | | | 3.0 | | | | | 3.0 |
| | Alkylene glycol ether 8 | | | | | | | | | | | | |
| | Alkylene glycol ether 9 | | | | | | | | | | | | |
| | Alkylene glycol ether 10 | | | | | | | | | | | | |
| | Alkylene glycol ether 11 | | | | | | | | | | | | |
| | Alkylene glycol ether 12 | | | | | | | | | | | | |
| | Alkylene glycol ether 13 | | | | | | | | | | | | |
| | Alkylene glycol ether 14 | | | | | | | | | | | | |
| | Alkylene glycol ether 15 | | | | | | | | | | | | |
| | Alkylene glycol ether 18 | | | | | | | | | | | | |
| Component (B) | Stearyl trimethyl ammonium chloride | 0.98 | 0.98 | 0.98 | 0.98 | 0.98 | 0.98 | 0.98 | 0.98 | 0.98 | 0.98 | 0.98 | 0.98 |
| | Dialkyl (C12 to C18) dimethyl ammonium chloride | 0.98 | 0.98 | 0.98 | 0.98 | 0.98 | 0.98 | 0.98 | 0.98 | 0.98 | 0.98 | 0.98 | 0.98 |
| Component (C) | Cetyl alcohol | 3.0 | 3.0 | 3.0 | 3.0 | 3.0 | 3.0 | 3.0 | 3.0 | 3.0 | 3.0 | 3.0 | 3.0 |
| | Stearyl alcohol | 3.0 | 3.0 | 3.0 | 3.0 | 3.0 | 3.0 | 3.0 | 3.0 | 3.0 | 3.0 | 3.0 | 3.0 |
| | Octyldodecyl myristate | | | | | | | | | | | | |
| | Polyglyceryl triisostearate | | | | | | | | | | | | |
| | Highly polymerized dimethylsiloxane methyl(aminopropyl)siloxane copolymer | | | | | | | | | | | | |
| | Branched polyglycerol modified silicone | | | | | | | | | | | 0.5 | 0.5 | 0.5 |
| | Dimethyl polysiloxane | | | | | | | | | | | 2.0 | 2.0 | 2.0 |
| | Hydroxyethylcellulose | 0.2 | 0.2 | 0.2 | 0.2 | 0.2 | 0.2 | 0.2 | 0.2 | 0.2 | 0.2 | 0.2 | 0.2 |

TABLE 4-continued

| | | Example | | | | | | | | | | | |
|---|---|---|---|---|---|---|---|---|---|---|---|---|---|
| | | 13 Pure content % | 14 Pure content % | 15 Pure content % | 16 Pure content % | 17 Pure content % | 18 Pure content % | 19 Pure content % | 20 Pure content % | 21 Pure content % | 22 Pure content % | 23 Pure content % | 24 Pure content % |
| | Component name | | | | | | | | | | | | |
| Others | Methylparaben | 0.3 | 0.3 | 0.3 | 0.3 | 0.3 | 0.3 | 0.3 | 0.3 | 0.3 | 0.3 | 0.3 | 0.3 |
| | Sodium 2-naphthalenesulfonate | | | | | | | | 0.5 | 0.5 | | | |
| | Purified water | Balance | Balance | Balance | Balance | Balance | Balance | Balance | Balance | Balance | Balance | Balance | Balance |
| Material | alcohol (ppm) | 12 | 45 | 27 | 15 | 12 | 12 | 12 | 45 | 68 | 12 | 15 | 12 |
| Evaluation | Hair manageability | 4.7 | 4 | 4.7 | 4 | 4.5 | 4.7 | 5 | 4.5 | 4 | 4.7 | 4.3 | 5 |
| | Moisturized feel | 5 | 5 | 5 | 4.7 | 5 | 5 | 5 | 5 | 4 | 5 | 4.7 | 5 |
| | Oily feel by hand transfer | 4.7 | 4.7 | 4.7 | 4.7 | 4.7 | 4.7 | 5 | 5 | 5 | 5 | 5 | 5 |
| | Odor evaluation | 3.7 | 3 | 3.3 | 3.7 | 4 | 4 | 3.7 | 3 | 3 | 3.7 | 3.7 | 4 |

Raw material name
Stearyl trimethyl ammonium chloride: Quartamin 86W (manufactured by Kao Corporation)
Dialkyl (C12 to C18) dimethyl ammonium chloride: Quartamin D2345P (manufactured by Kao Corporation)
Cetyl alcohol: Kalcol 6098 (manufactured by Kao Corporation)
Stearyl alcohol: Kalcol 8098 (manufactured by Kao Corporation)
Octyldodecyl myristate: Exceparl O-DM (manufactured by Kao Corporation)
Polyglyceryl triisostearate: Cosmol 43V (manufactured by Nisshin Oillio Group, Ltd.)
Highly polymerized dimethylsiloxane methyl(aminopropyl)siloxane copolymer: KF-8020 (manufactured by Shin-Etsu Chemical Co., Ltd.)
Hydroxyethylcellulose: HEC Daicel SE850 (manufactured by Daicel Chemical Industries Ltd.)
Polyglycerol modified polydimethylsiloxane: Sofcare GS-G (manufactured by Kao Corporation)
Dimethyl polysiloxane: BY22-060 (manufactured by Dow Corning Toray Co., Ltd.)

TABLE 5

| | | Comparative Example | | | | | | | |
|---|---|---|---|---|---|---|---|---|---|
| | | 12 Pure content % | 13 Pure content % | 14 Pure content % | 15 Pure content % | 16 Pure content % | 17 Pure content % | 18 Pure content % | 19 Pure content % |
| | Component name | | | | | | | | |
| Component (A) | Alkylene glycol ether 1 | | | | | | | | |
| | Alkylene glycol ether 2 | | | | | | | | |
| | Alkylene glycol ether 3 | | | | | | | | |
| | Alkylene glycol ether 4 | | | | | | | | |
| | Alkylene glycol ether 6 | | | | | | | | |
| | Alkylene glycol ether 7 | | | | | | | | |
| | Alkylene glycol ether 8 | | 3.0 | | | | | | |
| | Alkylene glycol ether 9 | | | 3.0 | | | | | |
| | Alkylene glycol ether 10 | | | | 3.0 | | | | |
| | Alkylene glycol ether 11 | | | | | 3.0 | | | |
| | Alkylene glycol ether 12 | | | | | | 3.0 | | |
| | Alkylene glycol ether 13 | | | | | | | 3.0 | |
| | Alkylene glycol ether 14 | | | | | | | | 3.0 |
| | Alkylene glycol ether 15 | | | | | | | | |
| | Alkylene glycol ether 18 | | | | | | | | |
| Component (B) | Stearyl trimethyl ammonium chloride | 0.98 | 0.98 | 0.98 | 0.98 | 0.98 | 0.98 | 0.98 | 0.98 |
| | Dialkyl (C12 to C18) dimethyl ammonium chloride | 0.98 | 0.98 | 0.98 | 0.98 | 0.98 | 0.98 | 0.98 | 0.98 |
| Component (C) | Cetyl alcohol | 3.0 | 3.0 | 3.0 | 3.0 | 3.0 | 3.0 | 3.0 | 3.0 |
| | Stearyl alcohol | 3.0 | 3.0 | 3.0 | 3.0 | 3.0 | 3.0 | 3.0 | 3.0 |
| | Octyldodecyl myristate | | | | | | | | |
| | Polyglyceryl triisostearate | | | | | | | | |
| | Highly polymerized dimethylsiloxane methyl(aminopropyl)siloxane copolymer | | | | | | | | |
| | Branched polyglycerol modified silicone | | | | | | | | |
| | Dimethyl polysiloxane | | | | | | | | |
| Others | Hydroxyethylcellulose | 0.2 | 0.2 | 0.2 | 0.2 | 0.2 | 0.2 | 0.2 | 0.2 |
| | Methylparaben | 0.3 | 0.3 | 0.3 | 0.3 | 0.3 | 0.3 | 0.3 | 0.3 |
| | Sodium 2-naphthalenesulfonate | | | | | | | | |
| | Purified water | Balance | Balance | Balance | Balance | Balance | Balance | Balance | Balance |
| | Material alcohol (ppm) | 0 | 810 | 12 | 780 | 900 | 150 | 5,700 | 1,500 |
| Evaluation | Hair manageability | 2 | 3 | 4 | 2 | 1 | 2 | 2 | 2 |
| | Moisturized feel | 2 | 2 | 3 | 2 | 2 | 2 | 1 | 1 |
| | Oily feel by hand transfer | 4.7 | 3 | 2 | 4.7 | 4.7 | 4.7 | 4.7 | 4.7 |
| | Odor evaluation | 4 | 1.7 | 4 | 1 | 1 | 1 | 1 | 1 |

TABLE 5-continued

| | | Comparative Example | | | | | | | |
|---|---|---|---|---|---|---|---|---|---|
| | Component name | 20 Pure content % | 21 Pure content % | 22 Pure content % | 23 Pure content % | 24 Pure content % | 25 Pure content % | 26 Pure content % | 27 Pure content % |
| Component (A) | Alkylene glycol ether 1 | | | | | | | | |
| | Alkylene glycol ether 2 | | | | | | 6.0 | | |
| | Alkylene glycol ether 3 | | | | | | | | |
| | Alkylene glycol ether 4 | | | | | | | | |
| | Alkylene glycol ether 6 | | | | | | | | |
| | Alkylene glycol ether 7 | | | | | | | | |
| | Alkylene glycol ether 8 | | | | | | | | |
| | Alkylene glycol ether 9 | | | | | | | | |
| | Alkylene glycol ether 10 | | | | | | | | |
| | Alkylene glycol ether 11 | | | | | | | | |
| | Alkylene glycol ether 12 | | | | | | | | |
| | Alkylene glycol ether 13 | | | | | | | 3.0 | |
| | Alkylene glycol ether 14 | | | | | | | | |
| | Alkylene glycol ether 15 | 3.0 | | | | | | | |
| | Alkylene glycol ether 18 | | 3.0 | | | | | | |
| Component (B) | Stearyl trimethyl ammonium chloride | 0.98 | 0.98 | 0.98 | 0.98 | 0.98 | 0.98 | 0.98 | 0.98 |
| | Dialkyl (C12 to C18) dimethyl ammonium chloride | 0.98 | 0.98 | 0.98 | 0.98 | 0.98 | 0.98 | 0.98 | 0.98 |
| Component (C) | Cetyl alcohol | 3.0 | 3.0 | 3.0 | 3.0 | 3.0 | 3.0 | 3.0 | 3.0 |
| | Stearyl alcohol | 3.0 | 3.0 | 3.0 | 3.0 | 3.0 | 3.0 | 3.0 | 3.0 |
| | Octyldodecyl myristate | | | 3.0 | | | | | |
| | Polyglyceryl triisostearate | | | | 3.0 | | | | |
| | Highly polymerized dimethylsiloxane methyl(aminopropyl)siloxane copolymer | | | | | 3.0 | | | |
| | Branched polyglycerol modified silicone | | | | | | | 0.5 | 0.5 |
| | Dimethyl polysiloxane | | | | | | | 2.0 | 2.0 |
| Others | Hydroxyethylcellulose | 0.2 | 0.2 | 0.2 | 0.2 | 0.2 | 0.2 | 0.2 | 0.2 |
| | Methylparaben | 0.3 | 0.3 | 0.3 | 0.3 | 0.3 | 0.3 | 0.3 | 0.3 |
| | Sodium 2-naphthalenesulfonate | | | | | | | | |
| | Purified water | Balance | Balance | Balance | Balance | Balance | Balance | Balance | Balance |
| | Material alcohol (ppm) | 4,500 | | | | | 90 | 5,700 | |
| Evaluation | Hair manageability | 2 | 2 | 4 | 4 | 4 | 3 | 3 | 3 |
| | Moisturized feel | 1 | 2 | 4 | 2 | 2 | 3 | 2 | 2 |
| | Oily feel by hand transfer | 4.7 | 4 | 2 | 1 | 2 | 4.7 | 3 | 2 |
| | Odor evaluation | 1 | 1.3 | 3.7 | 3.7 | 4 | 2 | 1 | 3.7 |

Raw material name
Stearyl trimethyl ammonium chloride: Quartamin 86W (manufactured by Kao Corporation)
Dialkyl (C12 to C18) dimethyl ammonium chloride: Quartamin D2345P (manufactured by Kao Corporation)
Cetyl alcohol: Kalcol 6098 (manufactured by Kao Corporation)
Stearyl alcohol: Kalcol 8098 (manufactured by Kao Corporation)
Octyldodecyl myristate: Exceparl O-DM (manufactured by Kao Corporation)
Polyglyceryl triisostearate: Cosmol 43V (manufactured by Nisshin Oillio Group, Ltd.)
Highly polymerized dimethylsiloxane methyl(aminopropyl)siloxane copolymer: KF-8020 (manufactured by Shin-Etsu Chemical Co., Ltd.)
Hydroxyethylcellulose: HEC Daicel SE850 (manufactured by Daicel Chemical Industries Ltd.)
Polyglycerol modified polydimethylsiloxane: Sofcare GS-G (manufactured by Kao Corporation)
Dimethyl polysiloxane: BY22-060 (manufactured by Dow Corning Toray Co., Ltd.)

From Tables 4 and 5, there are revealed that the hair conditioning composition of the present invention is excellent in oily feel by the hand transfer upon finish (the greasy feel is low) and can impart good smoothness and the good moisturized feel. The hair conditioning composition of the present invention has the low odor and good usability, and is also excellent in hair softness without impairing the voluminous look of the hair.

In Comparative Example 14 using alkylene glycol ether containing a large number of polyoxypropylene molecules, the oily feel by the hand transfer (greasy feel) was strong. In Comparative Examples 16 to 20 using alkylene glycol ether containing a large Number of polyoxyethylene molecules, there was neither the hair manageability nor the moisturized feel. In Comparative Example 21 using alkylene glycol ether containing $R^1$ having a small number of carbon atoms, the manageability and the moisturized feel were lacked and the odor was strong. In Comparative Examples 22 to 24, the voluminous look of the hair was inferior. Further, in the case of using alkylene glycol ether containing a large amount of material alcohol, the odor was strong, and the usabilities, e.g., the hair manageability and moisturized feel were inferior.

Example 25

A formulation example of the hair conditioner of the present invention is shown below.

TABLE 6

| Raw material name | Component name (major component) | Blended amount (% by weight) |
|---|---|---|
| Quartamin E-80K* | Octadecyloxypropyl trimethyl ammonium chloride (active content: 45% by weight) | 2.44 |

TABLE 6-continued

| Raw material name | Component name (major component) | Blended amount (% by weight) |
|---|---|---|
| Quartamin D2345P* | Dialkyl (C12 to C18) dimethyl ammonium chloride (active content: 75% by weight) | 1.12 |
| Kalcol 6098* | Cetyl alcohol | 2.5 |
| Kalcol 8098* | Stearyl alcohol | 2.5 |
| Alkylene glycol ether 7 | | 0.5 |
| BY22-050A** | Highly polymerized dimethylsiloxane (1) | 1.0 |
| SOFCARE GS-G* | Polyglycerol modified polydimethylsiloxane | 0.5 |
| HEC Daicel SE850*** | Hydroxyethylcellulose | 0.1 |
| Citric acid | Citric acid | 0.05 |
| Methylparaben | | 0.3 |
| Purified water | Purified water | 88.99 |

*Manufactured by Kao Corporation
**Manufactured by Dow Corning Tray Co., Ltd.
***Manufactured by Daicel Chemical Industries Ltd.

This conditioner had good feel upon application, was excellent in hair manageability and moisturized feel after washing off, and was not greasy in the finish.

What is claimed is:

1. A method of conditioning hair, which comprises:
washing said hair;
applying a hair conditioning composition to said hair; and
drying said hair without rinsing,
wherein the applied composition comprises a content of $R^1OH$, where $R^1$ represents a straight or branched, alkyl or alkenyl group having 8 to 12 carbon atoms, is 30 ppm or less, based on the composition, and the following components (A) and (B): wherein
component (A) is a compound represented by formula (1)

$$R^1O\text{---}(PO)_n/(EO)_m\text{---}R^2 \quad (1)$$

wherein
$R^1$ represents a straight or branched, alkyl or alkenyl group having 8 to 12 carbon atoms,
PO represents a propyleneoxy group,
EO represents an ethyleneoxy group,
an average addition mole number "n" represents a number of 1.5 to 3.0,
an average addition mole number "m" represents a number of 0 to 1.0, and
$R^2$ represents a hydrogen atom or a methyl group; and
component (B) is at least one non-ionic surfactant or cationic surfactant, wherein the non-ionic surfactant comprises polyoxyalkylene alkylether, and the cationic surfactant comprises a quaternary ammonium salt type cationic surfactant represented by formula (2)

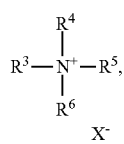
(2)

wherein one or two of $R^3$, $R^4$, $R^5$, and $R^6$ each represent a hydrocarbon group having 12 to 25 total carbon atoms, which may be interrupted with a functional group represented by —O—, —CONH—, NHCO—, —OCO—, or —COO—, or may be substituted with —OH and the remainder of $R^3$, $R^4$, $R^5$, and $R^6$ each independently represent an alkyl or a hydroxyalkyl group having 1 to 4 carbon atoms or a polyoxyethylene group, and X represents a halide ion or an organic anion,
wherein a weight ratio of the component (A) to the component (B), (A)/(B), ranges from 1/5 to 5/1, component (A) is present in an amount of 0.1 to 7% by weight, and component (B) is present in an amount of 0.1 to 7% by weight.

2. The method according to claim 1, wherein the composition further comprises a component (C) being an oily component.

3. The method according to claim 1, wherein a weight ratio of the component (A) to the component (B), (A)/(B), is 1/5 to 3/1.

4. The method according to claim 1, wherein a weight ratio of the component (A) to the component (B), (A)/(B), is 1/3 to 3/1.

5. The method according to claim 2, wherein a weight ratio of the component (A) to the component (C) [(A)/(C)] is 1/5 to 5/1.

6. The method according to claim 2, which wherein said composition is an emulsified product.

7. The method according to claim 1, wherein the composition further comprises, as a component (D), naphthalene sulfonic acid, oxybenzone sulfonic acid, or salts thereof.

8. The method according to claim 7, wherein a weight ratio of the component (D) to the component (A) [(D)/(A)] is 1/5 to 3/1.

9. The method according to claim 1, which improves manageability of hair.

10. A method of conditioning hair, which comprises:
washing said hair;
applying a hair conditioning composition to said hair;
rinsing said hair; and
drying said hair,
wherein the applied composition comprises a content of $R^1OH$, where $R^1$ represents a straight or branched, alkyl or alkenyl group having 8 to 12 carbon atoms, is 68 ppm or less, based on the composition, and the following components (A) and (B): wherein
component (A) is a compound represented by formula (1)

$$R^1O\text{---}(PO)_n/(EO)_m\text{---}R^2 \quad (1)$$

wherein
$R^1$ represents a straight or branched, alkyl or alkenyl group having 8 to 12 carbon atoms,
PO represents a propyleneoxy group,
EO represents an ethyleneoxy group,
an average addition mole number "n" represents a number of 1.5 to 3.0,
an average addition mole number "m" represents a number of 0 to 1.0, and
$R^2$ represents a hydrogen atom or a methyl group; and
component (B) is at least one non-ionic surfactant or cationic surfactant, wherein the non-ionic surfactant comprises polyoxyalkylene alkylether, and the cationic surfactant comprises a quaternary ammonium salt type cationic surfactant represented by formula (2)

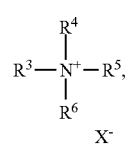
(2)

wherein one or two of $R^3$, $R^4$, $R^5$, and $R^6$ each represent a hydrocarbon group having 12 to 25 total carbon atoms, which may be interrupted with a functional group represented by —O—, —CONH—, NHCO—, —OCO—, or —COO—, or may be substituted with —OH and the remainder of $R^3$, $R^4$, $R^5$, and $R^6$ each independently represent an alkyl or a hydroxyalkyl group having 1 to 4 carbon atoms or a polyoxyethylene group, and X– represents a halide ion or an organic anion,
wherein a weight ratio of the component (A) to the component (B), (A)/(B), ranges from 1/5 to 5/1, component (A) is present in an amount of 0.1 to 7% by weight, and component (B) is present in an amount of 0.1 to 7% by weight.

11. The method according to claim 10, wherein the composition further comprises a component (C) being an oily component.

12. The method according to claim 10, wherein a weight ratio of the component (A) to the component (B), (A)/(B), is 1/5 to 3/1.

13. The method according to claim 10, wherein a weight ratio of the component (A) to the component (B), (A)/(B), is 1/3 to 3/1.

14. The method according to claim 11, wherein a weight ratio of the component (A) to the component (C) [(A)/(C)] is 1/5 to 5/1.

15. The method according to claim 11, which wherein said composition is an emulsified product.

16. The method according to claim 10, wherein the composition further comprises, as a component (D), naphthalene sulfonic acid, oxybenzone sulfonic acid, or salts thereof.

17. The method according to claim 16, wherein a weight ratio of the component (D) to the component (A) [(D)/(A)] is 1/5 to 3/1.

18. The method according to claim 10, which improves manageability of hair.

19. The method according to claim 1, wherein the polyoxyalkylene alkylether comprising the non-ionic surfactant of component (B) is a polyoxyalkylene alkylether other than the component (A).

20. The method according to claim 10, wherein the polyoxyalkylene alkylether comprising the non-ionic surfactant of component (B) is a polyoxyalkylene alkylether other than the component (A).

* * * * *

UNITED STATES PATENT AND TRADEMARK OFFICE
CERTIFICATE OF CORRECTION

PATENT NO. : 8,932,568 B2  
APPLICATION NO. : 12/933626  
DATED : January 13, 2015  
INVENTOR(S) : Juri Sata et al.

Page 1 of 1

It is certified that error appears in the above-identified patent and that said Letters Patent is hereby corrected as shown below:

In the Claims

At column 26, delete line 1 in its entirety and replace with the following:
--carbon atoms or a polyoxyethylene group, and $X^-$ repre- --

At column 27, delete line 8 in its entirety and replace with the following:
--carbon atoms or a polyoxyethylene group, and $X^-$ rep- --

Signed and Sealed this
Twelfth Day of May, 2015

Michelle K. Lee
*Director of the United States Patent and Trademark Office*